United States Patent [19]

Fumagalli et al.

[11] Patent Number: 4,713,464
[45] Date of Patent: Dec. 15, 1987

[54] PROCESS FOR PRODUCTION OF MALEIC ANHYDRIDE

[75] Inventors: Carlo Fumagalli, Valbrembo; Giancarlo Stefani, Bergamo, both of Italy

[73] Assignee: Alusuisse Italia, S.p.A., Milan, Italy

[21] Appl. No.: 819,599

[22] Filed: Jan. 27, 1986

Related U.S. Application Data

[62] Division of Ser. No. 789,151, Oct. 18, 1985, Pat. No. 4,668,652.

[30] Foreign Application Priority Data

Nov. 20, 1984 [IT] Italy ................................ 23671 A/84

[51] Int. Cl.$^4$ ........................................... C07D 307/60
[52] U.S. Cl. ..................................... 549/259; 549/260
[58] Field of Search ................................ 549/259, 260

[56] References Cited

U.S. PATENT DOCUMENTS 4,178,298 12/1979 Stefani et al. ...................... 549/260
4,520,127 5/1985 Otake et al. ........................ 549/260

OTHER PUBLICATIONS

J. S. Littler and W. A. Waters, J. Chem. Soc., (1959), pp. 1299 to 1305.
Koppel et al., Zeit. Anorg. Chem. 45, pp. 346 to 351, (1905).

Primary Examiner—Henry R. Jiles
Assistant Examiner—Bernard I. Dentz
Attorney, Agent, or Firm—Fisher, Christen & Sabol

[57] ABSTRACT

Catalyst containing a vanadium/phosphorus complex oxide, for the oxidation of hydrocarbons to maleic anhydride. The catalyst contains 1 to 1.3 atoms of phosphorus per atom of vanadium. The pore volume of those pores which have a radius of 100 to 1,000 Å is at least 30 percent of the total pore volume of the pores which have a radius of less than 10,000 Å. The method for preparing the catalyst involves introducing a phosphorus-containing compound into an organic solvent, and continuously adding a vanadium-containing compound over the course of 0.5 to 4 hours. 1 to 1.3 atoms of phosphous is employed per atom of vanadium. The water formed during the reaction is removed continuously and directly from the reaction mixture. Thereafter the reaction mixture is separated. The V-P-O complex oxide is isolated as a solid, dried at a temperature of 90° to 150° C. and activated at a temperature of 200° to 300° C. to provide the catalyst.

13 Claims, 1 Drawing Figure

PROCESS FOR PRODUCTION OF MALEIC ANHYDRIDE

This is a divisional of application Ser. No. 789,151, filed on Oct. 18, 1985 now U.S. Pat. No. 4,668,652.

BACKGROUND OF THE INVENTION

1. Field Of The Invention

The invention relates to a catalyst containing a vanadium/phosphorus complex oxide, for the partial oxidation of hydrocarbons to maleic anhydride. The invention also relates to a process for the preparation of such catalyst. The invention further relates to a reduction treatment for improving the performance of such catalyst.

2. Prior Art

It is known to employ V-P-O complex oxides as catalysts for the preparation of maleic anhydride from n-butane. As an example, it is known from U.S. Pat. No. 3,293,268 that a V-P-O complex oxide is prepared from an aqueous solution of hydrochloride acid using $V_2O_5$, $H_3PO_4$ and oxalic acid as raw materials. The V-P-O complex oxide is separated by evaporating the reaction mixture to dryness. After shaping and calcination of the V-P-O complex oxide, the molar yields obtained at a temperature of 550° to 575° C. are only 35 to 40 percent.

U.S. Pat. No. 4,100,106 reports an improvement. The V-P-O complex oxide is precipitated from the concentrated hydrochloride aqueous solution by addition of water. This permits obtaining a crystalline product, characterized by X-rays, which after proper conditioning affords molar yields of about 55 percent at 400° to 420° C. when utilized as a catalyst in the oxidation of butane to maleic anhydride. This procedure also has the drawback of employing highly corrosive hydrochloric acid.

The reduction of $V_2O_5$ with organic compounds has been well-known for some time: J. S. Littler and W. A. Waters, J. Chem. Soc., (1959), pages 1299 to 1305. Concerning the reduction of $V_2O_5$ in alcoholic solutions containing HCl; see Koppel et al., Zeit. Anorg. Chem. 45, pages 346 to 351 (1905).

U.S. Pat. No. 3,864,280 describes the preparation of a V-P-O complex oxide in organic solvent in the presence of gaseous HCl. Once the reduction of $V_2O_5$ is terminated, $H_3PO_4$ is added and the V-P-O complex oxide is separated by evaporation of the organic solvent. The V-P-O complex oxide is conditioned according to a very strict procedure up to 480° C. and transformed into a crystalline phase called "phase B", which represents the active catalyst. The conditioning phase of this catalyst is of utmost importance for the results of its performances and must be carried out following a procedure that is not easy to realize industrially (i.e., increase in temperature by 3° C./min.). Further, this patent describes an intrinsic surface of the catalyst of from about 7 to 50 $m^2/g$ and states that the higher the intrinsic surface area, the more active is the catalyst.

West German Patent Application OS No. 3,010,710 reports the preparation of a V-P-O complex oxide in an organic solvent: the $V_2O_5$ reduction to vanadium IV is performed in the presence of $H_3PO_4$. All of the reagents are added to the organic solvent at the beginning of the operation. The catalyst thusly obtained requires a very long activation: the best performances are obtained only after 10 to 20 days, with loss in production capacity.

In all methods of preparation of the V-P-O complex oxides reported up to the present time, the vanadium V compound is present in the reaction mixture from the beginning. In some cases, the phosphorus compound is added at the end of the reduction of the vanadium V to vanadium IV. In some other cases, it is present in the reaction mixture since the beginning.

BROAD DESCRIPTION OF THE INVENTION

An object of the invention is to provide a catalyst which is distinguished, as compared to known catalysts, by easier and more rapid conditioning and especially by higher activity, selectivity and productivity. Another object of the invention is to provide a process for the preparation of such catalyst. Other objects and advantages of the invention are set out herein or are obvious herefrom to one skilled in the art.

The objects and advantages of the invention are achieved by the catalyst and processes of the invention.

The catalyst according to the invention is characterized in that the pore volume of those pores which have a radius of 100 to 1,000 Å is at least 30 percent of the total pore volume of the pores which have a radius of less than 10,000 Å.

Preferably, the pore volume of the pores which have a radius of 100 to 1,000 Å is at least 40 percent of the total pore volume of the pores which have a radius of less than 10,000 Å. More preferably, the percentage of the pore volume of the pores which have a radius of 100 to 1,000 Å tends toward 100 percent of the total pore volume of the pores which have a radius of less than 10,000 Å.

After preparing the V-P-O complex oxide and before trade in a ready-made catalyst, the V-P-O complex oxide is in the form of a finely distributed powder. In accordance with the invention, 90 percent of the particles of the powder have a diameter of about 1 to 5 micrometers and an average diameter of 2 to 4 micrometers.

The only pores having a radius less than 10,000 Å have been considered in the definition of pore volume because larger pores have no importance being of the same order of magnitude as the particles themselves, since 1 micrometer corresponds to 10,000 Å. The pore volume is measured by means of the well-known Mercury Penetration Porosimetry.

The high percentage of pores which have a radius of 100 to 1,000 Å, as is to be found in the catalyst according to the invention, leads to catalyst characteristics—for example, in the oxidation of n-butane to maleic anhydride—which are far superior to those of known catalysts. It has also been found that, for the catalyst performance, the pore size and pore size distribution of the invention are superior over a large intrinsic surface.

The catalyst according to the invention shows a high selectivity, a high activity and a uniformly high productivity. Thus, the invention catalyst can be operated over very long periods of time, without losses of performance, under high specific feed rates, which can for example be up to 150 grams of n-butane per hour per kilogram of catalyst, with high yields of almost 100 kg of maleic anhydride per 100 kg of butane feed, which corresponds to a hourly maleic anhydride production rate of 150 grams per kg of catalyst.

Operating with lower specific hydrocarbon (e.g., n-butane) feed rates, yields by weight of up to 110 percent can be obtained with the invention catalyst.

In an advantageous embodiment, the catalyst contains 1 to 1.3, preferably 1.05 to 1.2, atoms of phosphorus per atom of vanadium. Moreover, the catalyst can also contain one or more promoting agents from the group comprised of Li, Ti, Zr, Hf, Cr, Mo, Mn, Fe, Co, Ni, Cu, Zn, B, Si, Sn and Bi.

The process according to the invention is characterized in that a phosphorus-containing compound is introduced into an organic solvent, a vanadium-containing compound is added continuously over the course of 0.5 to 4 hours, preferably 0.8 to 2 hours, 1 to 1.3 atoms of phosphorus being employed per atom of vanadium, and the water formed during the reaction is removed continuously and directly from the reaction mixture. Thereafter, the reaction mixture is separated and the V-P-O complex oxide is isolated as a solid, dried at a temperature of 90° to 150° C., preferably 130° to 140° C., and activated at a temperature of 200° to 300° C. to provide the catalyst.

The catalyst has a well defined crystalline structure which is characterized by the following X-Ray diffraction spectrum (CuK):

TABLE A

| d-values (Angstrom) | Intensity | d-values (Angstrom) | Intensity |
|---|---|---|---|
| 5.83 | VW | 2.65 | W |
| 5.65 | VS | 2.60 | W |
| 4.79 | W | 2.55 | VVW |
| 4.53 | VS | 2.44 | VVW |
| 4.08 | W | 2.39 | W |
| 3.68 | M | 2.25 | VVW |
| 3.29 | M | 2.22 | W |
| 3.10 | M | 2.20 | VVW |
| 2.95 | VVW | 2.12 | VW |
| 2.94 | VS | 2.10 | VVW |
| 2.78 | M | 2.04 | VW |

Notes:
VS = very strong
S = strong
M = medium
W = weak
VW = very weak
VVW = very very weak After activation, the catalyst can be used as is. Preferably a reducing-treatment of the catalyst is carried out. This reducing-treatment is carried out by placing the catalyst in gaseous hydrocarbons with 2 to 6 C atoms, suitably a composition, comprising n-butane, 1,3-butadiene, n-butene, 1-butene, cis-2-butene, trans-2-butene or mixtures thereof and advantageously n-butane, in the absence of molecular oxygen at a temperature of 300° to 500° C.

In another embodiment the gaseous hydrocarbon contains an inert gas, preferably $CO_2$ or $N_2$.

The reduction-treatment of the invention catalysts gives a higher performance for new catalysts and for long used catalysts, showing a loss in conversion and yield, a full recover to the starting performance. The reduction treatment can take place either in the reactor with the built-in catalyst or, after removing the catalyst, in a separate device.

A $C_1$–$C_6$-alcohol, preferably methanol, ethanol, propanol, butanol, 1-propanol, 2-propanol, 1-butanol, 2-butanol, isobutanol, iso-amyl alcohol or mixtures thereof, and more preferably isobutanol, can be employed as the organic solvent.

Suitable phosphorus-containing compounds are those of pentavalent phosphorus, advantageously $P_2O_5$ or 85 percent by weight $H_3PO_4$ and preferably 100 percent by weight $H_3PO_4$.

Organic and/or inorganic compounds of tetravelent and/or petavalent vanadium and preferably $V_2O_5$, can be used as the vanadium-containing compounds. The form of the vanadium compound is an important factor in the quality of the catalyst. Improved results are achieved with a powdered vanadium compound, of which the particle diameter should be 1 micrometer or less. Such fine powders can be obtained, for example, by milling in a jet mill.

The vanadium and phosphorus components are employed in an atomic ratio P/V of between 1:1 and 1.3:1, preferably 1.05:1 to 1.2:1.

A number of promoting agents can be added to the catalyst during the process of preparation or before molding the finished catalyst. The promoting agent can be Li, Ti, Zr, Hf, Cr, Mo, Mn, Fe, Co, Ni, Cu, Zn B, Si, Sn or Bi, which can be used individually or as a mixture with one another. If a promoting agent is used, the ratio of the latter to vanadium is 0.01:1 to 0.3:1, preferably 0.05:1 to 0.15:1. The above-mentioned promoting agents or promoters can be used as their oxides or salts and in the latter case advantageously as a carbonate, nitrate, chloride, bromide, sulfate or acetate.

The catalyst can be prepared, for example, by introducing the solvent and the phosphorus compound into a reactor which is equipped with a stirring apparatus, a distillation column with a condenser and a water separator. The amount of solvent relative to the phosphorus is advantageously 5 to 50 kg, preferably 10 to 20 kg, of solvent per kg of phosphorus.

The mixture is heated to the boiling point and the vanadium compound, as a solid or as a suspension in a suspending medium which as a rule corresponds to the solvent mentioned, is added slowly, over a period of 0.5 to 4 hours, preferably 0.8 to 2 hours, with stirring, to the reactor. During this process step the valence of the vanadium is reduced to less than 5 and the water formed in the reaction is removed by means of the water separator. When the addition of vanadium has been completed, the reaction mixture is kept under reflux for a further 1 to 2 hours and the water formed is continuously removed. The final valence of the vanadium is 3.9 to 4.2.

The suspension containing the V-P-O complex oxide is then cooled.

The V-P-O complex oxide formed can be separated off by filtration and subsequent drying. Alternatively, the solvent can be evaporated to reduce the mixture of dryness, with the solid, dried V-P-O complex oxide resulting in both cases. A further suitable embodiment is, for example, to aim at a 40 to 50 percent solids concentration of the suspension by evaporating off or distilling off the solvent. This slurry-like reaction mixture then is processed further by spray-drying, if appropriate with the aid of binders.

The V-P-O complex oxide drying temperature is in each case advantageously 90° to 150° C., preferably 130° to 140° C.

The last-mentioned method if isolating the V-P-O complex oxide from the reaction mixture is particularly suitable if the solid is to be molded, for example, tableted for use in fixed bed reactors. The spray drying gives powders having excellent flow properties, which can easily be converted to tablets having very homogeneous properties. Other shaping systems which may be employed are, for example, extrusion or tableting by means of a granulating tray or granulating drum.

The catalyst can be molded before or after activation, the sequence of activation and molding not being critical per se. Activation is affected by heating to a temperature fo 200° to 300° C. and as a rule requires 2 to 24 hours.

As mentioned above, the catalyst according to the invention can be shaped for use in a fixed bed reactor or can also be treated appropriately, e.g., by spray-drying, to be used in a fluidized bed reactor.

The catalyst according to the invention is used for the oxidation of 1,3-butadiene, n-butane, n-butene, but-1-ene, cis-but-2-ene, trans-but-2-ene and mixtures thereof, to maleic anhydride. Preferably the catalyst according to the invention is used for the partial oxidation of n-butane to maleic anhydride.

DETAILED DESCRIPTION OF THE INVENTION

Figure 1:
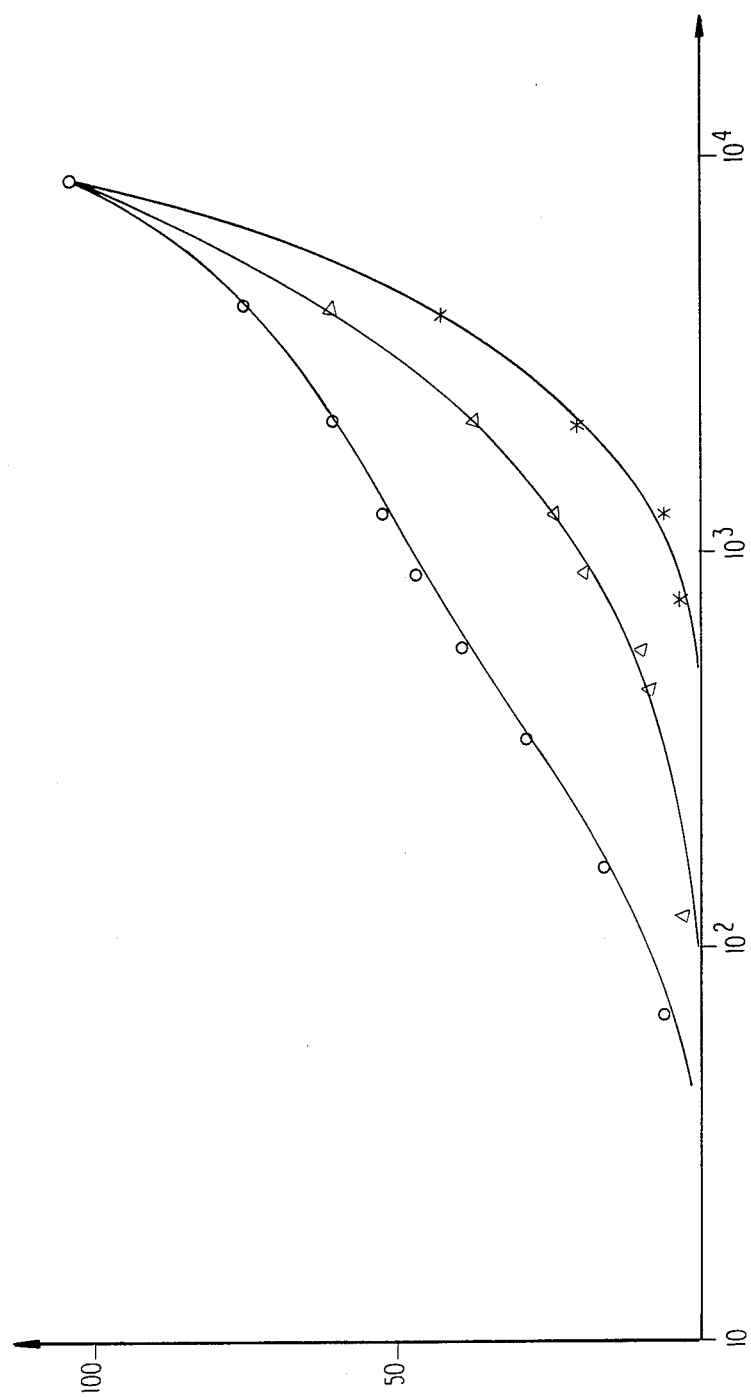
FIG. 1 shows the pore volume distribution for the pores having a radius smaller than 10,000 Å of V-P-O complex oxides, dried at 140° C. The abscissa represents the radius in Å and the ordinate the percent pore volume.

In FIG. 1, the line represented by the symbol "o" is for a V-P-O complex oxide prepared according to the invention (see Example 1), the line represented by the symbol "*" is for a V-P-O complex oxide prepared according to U.S. Pat. No. 4,100,106 (Comparative Example 1), and the line represented by the symbol "v" is for a V-P-O complex oxide prepared in isobutanol, all of the $V_2O_5$ having been added at the beginning (see Comparative Example 2).

As used in the following examples and elsewhere herein, all parts, percentages, ratios and proportions are on a weight basis unless otherwise obvious to one skilled in the art or otherwise stated herein.

REACTORS UTILIZED

Three types of reactors have been used to study the performance of the catalysts:

Reactor A: reactor $\phi i = 25$ mm, height of catalyst bed = 90 mm, the reaction tube is inserted in an aluminum block heated by an electric coil.

Reactor B: reactor $\phi i = 21$ mm, height of catalyst bed = 3000 mm, the tube is immersed in a molten salts bath heated by an electric coil.

Reactor C: reactor $\phi i = 25$ mm, height of catalyst bed = 3000 mm, the tube is immersed in a molten salts bath heated by an electric coil.

The three reactors may be fitted with internal axial thermowell to record the reaction temperatures.

Hereinafter, the performance of the catalysts are characterized by the following parameters:

percent hydrocarbon conversion =

$$\frac{\text{mols of hydrocarbon converted to products}}{\text{moles of hydrocarbon fed}} \cdot 100$$

percent weight yield = $\frac{\text{g of maleic anhydride produced}}{\text{g of hydrocarbon fed}} \cdot 100$ percent weight selectivity =

$$\frac{\text{g of maleic anhydride produced}}{\text{g of hydrocarbon converted to products}} \cdot 100$$

EXAMPLE 1

Into a three-necked flask, capacity 5 liters, fitted with thermometer, mechanical stirrer, glass distillation packed column with reflux condenser and Dean-Stark water separator, are introduced 2 liters of isobutanol and 404 of $H_3PO_4$ (100 percent). The mixture is brought to reflux and then a suspension of 326 g of $V_2O_5$ in 1000 cc. of isobutanol is slowly added (in about 1 hour). During addition of the $V_2O_5$, a quantity of isobutanol equal to that added with the $V_2O_5$ is distilled thus removing from the reaction mixture the water that forms during the reaction of the $V_2O_5$. At the end of the addition of the $V_2O_5$ the reflux is continued for another two hours, thus separating further reaction water. The slurry is cooled and the blue solid is filtered and dried at 140° C. In this manner the V-P-O complex oxide precursor of the catalyst is obtained.

The distribution of the pores of the resultant powder is such that the volume of the pores which have a radius between 100 and 1,000 Å is 36 percent of the total volume of the pores below 10,000 Å. This is shown in FIG. 1 where the distribution of the volume of the pores is compared with that of other precursors obtained according to the prior art (see Comparative Examples 1 and 2). The dry powder is tableted into cylinders of $\phi = 3$ mm, h = 3 mm, using stearic acid as an additive. The cylinders are calcined at 300° C. for 6 hours.

300 g of catalyst is charged into a laboratory reactor type A at 300° C. The catalyst is heated up to 350° C. in an air stream (500 Nl/h), increasing the temperature by 20° C./h, and then n-butane is added to the feed at a 13 g/h rate. In two hours time the temperature is brought to 380° C. and let stand under these conditions for 16 hours. At this point the catalyst affords optimal and constant performance.

Table 1 reports the catalyst performance during the test:

TABLE 1

| Run, Hours | Reactor Temp., °C. | C4-conversion, % | Yield, wt. % | Selectivity, wt. % |
|---|---|---|---|---|
| 16 | 380° | 90 | 110 | 122 |
| 540 | 370° | 89 | 108 | 121 |
| 960 | 375° | 91 | 109 | 120 |

EXAMPLE 2

The procedure is the same as that described for Example 1. Into a AISI 316 stainless steel reactor (capacity 400 liters) fitted with stirrer, packed distillation column and water separator, are introduced 250 liters of isobutanol and 38.7 kg of 100 percent of phosphoric acid. A suspension of 31.3 kg of $V_2O_5$ in 100 liters of isobutanol is added in about 1 hour. During the addition of this suspension, an equal amount of isobutanol is distilled, removing from the raction mixture the water that forms during the reaction of the $V_2O_5$. At the end of this operation the reflux is continued for another 2.5 hours, thereby separating further reaction water. The slurry containing the V-P-O complex oxide is concentrated by distilling the isobutanol. When the suspension reached a 35 weight percent solid content, it is cooled down and spray-dried utilizing an apparatus apt to recover the solvent.

The resulting microspheroidal product is submitted to a thermal pre-treatment at 280° C. for 12 hours in air. Stearic acid is added to the solid which is then tableted (cylinders 4×4 mm). The tablets are charged into a reactor type B at a temperature of 300° C. The temperature is gradually increased up to 370° C., feeding air; at 370° C., n-butane is added to the feed gradually reaching the operational-conditions (space velocity, 3200 $h^{-1}$; n-butane concentration, 1.8 mol percent).

After 8000 hours the catalyst is submitted to an activation treatment as described in U.S. Pat. No. 4,181,628: a n-butane-nitrogen mixture (50 percent vol. of n-butane) is fed to the reactor for 12 hours at 430° C.

After this treatment the performance of the catalyst is: salt temperature, 400° C.; conversion, 83 percent; weight yield, 97 percent; and weight percent selectivity, 117 percent.

The catalyst performance is reported in Table 2:

TABLE 2

| Run, Hours, | Salt Temperature, °C. | C4 conversion, % | Yield, wt. % | Selectivity, wt. % |
|---|---|---|---|---|
| 120 | 410° | 81 | 98 | 121 |
| 720 | 407° | 82 | 99 | 121 |
| 1250 | 405° | 80 | 97 | 121 |
| 4250 | 407° | 83 | 98 | 118 |
| 7680 | 407° | 85 | 93 | 109 |

EXAMPLE 3

The procedure is the same as that described for Example 2. At the end of the reaction the V-P-O complex oxide is filtered using a pressure filter. The filtration cake is dried at 80° C. in a vacuum dryer and granulated after adding stearic acid. The granules obtained are milled and the fraction of solids with sizes ranging between 50 and 300 microns is tableted into ring-shaped tablets, 5×4×1.5 mm (external diameter x height x thickness). After thermal pre-treatment at 320° C. for 7 hours in air, the tablets are charged into a reactor type C at 300° C. The oeprational conditions are gradually established: space velocity, 2300 $h^{-1}$; n-butane concentration, 1.8 mol percent.

The catalyst performance is reported in Table 3.

TABLE 3

| Run, Hours, | Salt Temperature, °C. | C4 conversion, % | Yield, wt. % | Selectivity, wt. % |
|---|---|---|---|---|
| 130 | 398° | 85 | 102 | 120 |
| 800 | 395° | 87 | 104 | 120 |
| 1200 | 395° | 85 | 104 | 122 |
| 4000 | 397° | 86 | 103 | 120 |

EXAMPLE 4

A V-P-O complex oxide is prepared, shaped and calcined as described in Example 1. 300 g of the cylinders (φ3 mm, h 3 mm) is charged into a laboratory reactor type A at 300° C. Reaction conditions are gradually established as follows:
air flow: 500 nl/h
C4 cut feed: 15 g/h
reactor temperature: 365° C.
The composition of the C4 cut is:
n-butane: 18%
isobutane: 5%
1-butene: 55%
cis-2-butene: 7%
trans-2-butene: 15%
After 12 hours the catalytic performance is stabilized:
C4 conversion: 91%
wt. yield referred to total C4: 90%

EXAMPLE 5

A catalyst is prepared and formed in microspheres (average size 100 micron) by spray-drying as described in Example 2. The microspheres are submitted to a thtermal pre-treatment at 250° C. for 8 hours in air.

500 g of this catalyst is charged into a glass laboratory fluid bed reaction (φi=40 mm). The temperature is gradually increased up to 370° C., feeding air; at 370° C., n-butane is added to the feed gradually reaching the reaction conditions: air flow, 150 Nl/h; n-butane concentration, 5 percent mol.

After 10 hours the performance is steady: reactor temperature, 380° C.; n-butane conversion, 75 percent, weight percent yield, 92 percent.

COMPARATIVE EXAMPLE 1

A V-P-O complex is prepared according to Example 1 of U.S. Pat. No. 4,100,106.

1000 mg of $V_2O_5$ is suspended in 8000 mg of 36 percent HCl (aqueous solution). The suspension is heated carefully, while stirring, to 100° C. and is boilded for 2 hours under reflux. Then 70 mg of anhydrous oxalic acid, dissolved in 700 ml of water, is added slowly, and finally 1370 mg of 85 percent $H_3PO_4$ is added. This mixture is concentrated to a volume of about 2000 ml and then 2000 ml of water is added to the viscous solution obtained in that way. A blue crystalline precipitate is obtained. The solid is filtered and dried.

The distribution of the pores of the powder is shown in FIG. 1: the pores which have a radius between 100 and 1,000 Å is only 4 percent of the total volume of the pores below 10,000 Å.

COMPARATIVE EXAMPLE 2

A V-P-O complex is prepared introducing all the vanadium compound at the beginning of the preparation. A mixture of 2 liters of isobutanol, 404 g of $H_3PO_4$ (100 percent) and 326 g of $V_2O_5$ is heated to reflux for 10 hours, removing from the reaction mixture the water that forms during the reduction of the $V_2O_5$ and the formation of the V-P-O complex. The slurry is cooled and the solid is filtered and dried at 130° C. The distribution of the pores of the powder is shown in FIG. 1: the pores having a radius between 100 and 1,000 Å is only 18 percent of the total volume of the pores below 10,000 Å. The dry powder is shaped into cylinders (φ 3 mm, h 3 mm) and calcined at 300° C. for 6 hours.

300 g of the catalyst is charged into a type A reactor and activated as described in Example 1. The catalyst reaches the best performance (88 percent conversion and 98 percent weight yield, reactor temperature 380° C.) only after 360 hours of operation.

What is claimed is:

1. The method comprising partially oxidizing 1,3-butadiene, n-butane, but-1-ene, cis-but-2-ene, trans-but-2-ene or a mixture of at least two of said compounds, to maleic anhydride in the presence of a catalyst, said catalyst consisting of a vanadium/phosphorus complex oxide, the catalyst containing 1 to 1.3 atoms of phosphorus per atom of vanadium, the catalyst having pores, the pore volume of those pores which have a radius of 100 to 1,000 Å is at 30 percent of the total pore volume of the pores which have a radius of less than 10,000 Å, the catalyst being produced by the method comprising introducing a phosphorus-containing compound into an organic solvent, continuously adding a vanadium-containing compound to the reaction mixture over the course of 0.5 to 4 hours, 1 to 1.3 atoms of phosphorus being employed per atom of vanadium, continuously removing the water formed during the reaction directly from the reaction mixture, separating the reaction mixture, removing the solvent from the formed V-P-O complex oxide at a temperature of 90° to 150° C. and activating the V-P-O complex oxide at a temperature of 200° to 300° C. to provide the catalyst.

2. Method according to claim 1 wherein the pore volume of the pores which have a radius of 100 to 1,000 Å is at least 40 percent of the total pore volume of the pores which have a radius of less than 10,000 Å.

3. Method according to claim 1 wherein the catalyst contains 1.05 to 1.2 atoms of phosphorus per atom of vanadium.

4. Method according to claim 1 wherein the catalyst, after activation or for reactivation thereof, is reduced by passing over the complex oxide a gaseous hydrocarbon component which has 2 to 6 carbon atoms, in the absence of molecular oxygen, at a temperature of 300° to 500° C.

5. Method according to claim 1 wherein n-butane is partially oxidized.

6. Method according to claim 1 wherein the catalyst is in a shaped form.

7. The method comprising partially oxidizing 1,3-butadiene, n-butane, but-1-ene, cis-but-2-ene, trans-but-2-ene or a mixture of at least two of said compounds, to maleic anhydride in the presence of a catalyst, said catalyst consisting of a vanadium/phosphorus complex oxide and a promoting agent selected from the group consisting of Li, Ti, Zr, Hf, Cr, Mo, Mn, Fe, Co, Ni, Cu, Zn, B, Si, Sn, Bi and a mixture of at least two of such metals, the proportion of the promoting agent to the vanadium being 0.01 to 0.3 atom of promoting agent per atom of vanadium, the catalyst containing 1 to 1.3 atoms of phosphorus per atom of vanadium, characterized in that the pore volume of those pores which have a radius of 100 to 1,000 Å is at least 30 percent of the total pore volume of the pores which have a radius of less than 10,000 Å, the catalyst being produced by the method comprising introducing a phosphorus-containing compound into an organic solvent, continuously adding a vanadium-containing compound to the reaction mixture over the course of 0.5 to 4 hours, adding a promoter agent-containing compound to the reaction mixture during the addition period of the vanadium-containing compound, continuously removing the water formed during the reaction directly from the reaction mixture, separating the reaction mixture, removing the solvent from the formed catalyst precursor of the V-P-O complex oxide and promoting agent at a temperature of 90° to 150° C. and activating the catalyst precursor at a temperature of 200° to 300° C. to provide the catalyst.

8. Method according to claim 7 wherein the pore volume of the pores which have a radius of 100 to 1,000 Å is at least 40 percent of the total pore volume of the pores which have a radius of less than 10,000 Å.

9. Method according to claim 7 wherein the catalyst contains 1.05 to 1.2 atoms of phosphorus per atom of vanadium.

10. Method according to claim 7 wherein the promoting agent compound is a carbonate, nitrate, chloride, bromide, sulfate, acetate or oxide.

11. Method according to claim 7 wherein the catalyst, after activation or for reactivation thereof, is reduced by passing over the complex oxide a gaseous hydrocarbon component which has 2 to 6 carbon atoms, in the absence of molecular oxygen, at a temperature of 300° to 500° C.

12. Method according to claim 7 wherein n-butane is partially oxidized.

13. Method according to claim 7 wherein the catalyst is in a shaped form.

* * * * *

UNITED STATES PATENT AND TRADEMARK OFFICE
CERTIFICATE OF CORRECTION

PATENT NO. : 4,713,464

DATED : December 15, 1987

INVENTOR(S) : Fumagalli et al.

It is certified that error appears in the above-identified patent and that said Letters Patent is hereby corrected as shown below:

On the Title Page, Item [22] should read:

[22] Filed: Jan. 17, 1986

Signed and Sealed this

Seventeenth Day of May, 1988

Attest:

DONALD J. QUIGG

*Attesting Officer*    *Commissioner of Patents and Trademarks*